Figure 1:
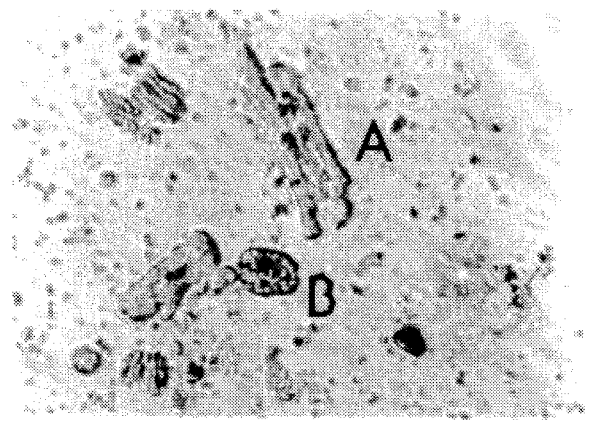

United States Patent [19]

Smith et al.

[11] Patent Number: 5,580,779

[45] Date of Patent: Dec. 3, 1996

[54] METHOD FOR INDUCING HUMAN MYOCARDIAL CELL PROLIFERATION

[76] Inventors: David A. Smith, 3244 Belle Ct., Royal Oak, Mich. 48073; Laurace Townsend, 868 Whittier Rd., Grosse Point Park, Mich. 48230; Dawn Newman; Ronald G. Duff, both of 67 Inlet View Path, East Moriches, N.Y. 11940

[21] Appl. No.: 416,931

[22] Filed: Apr. 4, 1995

Related U.S. Application Data

[63] Continuation of Ser. No. 286,402, Aug. 5, 1994, which is a continuation of Ser. No. 713,949, Jun. 12, 1991, each, abandoned.

[51] Int. Cl.⁶ ............................. C12N 5/00; A61K 35/14
[52] U.S. Cl. .................. 435/240.2; 435/240.21; 435/240.3; 424/529; 424/532
[58] Field of Search ........................... 435/240.2, 240.21, 435/240.3; 424/529, 532

[56] References Cited

U.S. PATENT DOCUMENTS

| 4,350,687 | 9/1982 | Lipton et al. | 424/177 |
| 4,479,896 | 10/1984 | Antoniades | 260/112 |

FOREIGN PATENT DOCUMENTS

| 9104035 | 4/1991 | WIPO | 424/532 |

OTHER PUBLICATIONS

Kardami, Molecular & Cellular Biochemistry, vol. 92, pp. 129–135 (1990).
Steinhelper et al, Amer. J. of Physiology, 259(6) Part 2 of 3 parts, issued Dec. 1990, pp. H1826–H1834.
Sen et al. J. of Biological Chemistry, 263(35) issued Dec. 15, 1988, pp. 19132–19136.
Blagosklonnyi et al., 1984, "Effect of platelet extract and platelet–poor plasma on the proliferative activity of connective tissue cells," Fiziol. Chel., 10(4):676–678 (Boisis Abstract No. 7974203).
Chang and Cumming, 1972, "Chronotropic responses of human heart tissue cultures," Circulation Research 30:628–633.
Claycomb et al., 1989, "Culture and characterization of fetal human atrial and ventricular cardiac muscle cells," In Vitro Cell. Dev. Biol. 25:1114–1120.
de Bold, 1985, "Atrial natriuretic factor: A hormone produced by the heart," Science 230:767–770.
Flynn and Davies, 1985, "The biochemistry and molecular biology of atrial natriuretic factor," Biochem. J. 232:313–321.
Follmer et al., 1987, "Sodium current kinetics in cat atrial myocytes," J. Physiol., 384:169–197.
Friedman et al., 1987, "The effect of hypoxia on thallium kinetics in cultured chick myocardial cells," J. Nuc. Med., 28(9):1453–1460.

Garrey and Townsend, 1948, "Neural responses and reactions of the heart of a human embryo," Amer. J. Phsyiol. 152(2):219–224.
Halbert et al., 1973, "Growth of dissociated beating human heart cells in tissue culture," Life Sciences 13:969–975.
Harary and Farley, 1963, "In vitro studies on single beating rat heart cells," Exp. Cell Res., 29:451–465.
Jacobson et al., 1985, "Long–term primary cultures of adult human and rat cardiomyocytes," Basic Res. Cardiol., 80, Suppl 1:79–82.
Kardami, 1990, "Stimulation and inhibition of cardiac myocyte proliferation in vitro," Mol. Cell. Biochem., 92:129–135.
Kohtz et al., 1989, "Growth and partial differentiation of presumptive human cardiac myoblasts in culture," J. Cell. Biol., 108:1067–1078.
Nag et al., 1983, "Long–term cell culture of adult mammalian cardiac myocytes: Electron microscopic and immunofluorescent analyses of myofibrillar structure," J. Mol. Cell. Cardiol., 15:301–317.
Nakajima et al., 1989, "Anti–cholinergic effects of quinidine, disopyramide, and procainamide in isolated atrial myocytes: Mediation by different molecular mechanisms," Circulation Research 64(2):297–303.
Rumyantsev, 1974, "Ultrastructural reorganization, DNA Synthesis and mitotic division of myocytes in atria of rats with left ventricle infarction," Virchows Arch. Abt. B. Zellpath., 15:357–378.

(List continued on next page.)

Primary Examiner—Michael G. Wityshyn
Assistant Examiner—Susan M. Dadio
Attorney, Agent, or Firm—Harness, Dickey & Pierce, P.L.C.

[57] ABSTRACT

The present invention relates to a method for inducing myocardial cell proliferation. It is based, at least in part, on the discovery that adult human myocardial cells may be induced to proliferate in culture by exposure to a platelet freeze/thaw extract. The present invention provides for a method for inducing myocardial cell proliferation in vitro, as well as for myocardial cell cultures produced by this method. In a preferred embodiment, the invention provides for human myocardial cell cultures. The myocardial cell cultures of the invention may be used to study the physiology of cardiac muscle. In addition, they may be used to identify pharmaceutical agents that may be useful in the treatment of heart disease or, alternatively, agents that are cardiotoxic. Furthermore, the cultures of the invention may be used to provide myocardial cells that may be transplanted or implanted in a patient that suffers from a cardiac disorder. In further embodiments, the present invention also provides for a method for inducing myocardial cell proliferation in vivo. Such methods may be used in the treatment of patients suffering from cardiac disorders, particularly those who have suffered damage or loss of cardiac muscle tissue.

4 Claims, 5 Drawing Sheets

OTHER PUBLICATIONS

Sato, 1980, "Effect of various growth substances on cultured endothelial cells," J. Kurume Med. Assoc., 43(12):992–1011 (Biosis Abstract No. 72079000).

Sen et al., 1988, "Terminally differentiated neonatal rat myocardial cells proliferate and maintain specific differentiated functions following expression of SV40 large T antigen," J. Biol. Chem. 263(35):19132–19136.

Severs, 1989, "Constituent cells of the heart and isolated cell models in cardiovascular research," in isolated adult cardiomyocytes, H. M. Piper and G. Isenberg eds., vol. 1, Boca Raton, CRC Press, pp. 3–41.

Smith et al., 1991, "A method for the harvest culture and characterization of human adult atrial myocardial cells correlation with age of donor," In Vitro Cell. Dev. Biol., 27A(12):914–920 (Biosis Abstract No. 93074055).

Steinhelper et al., 1990, "Proliferation in vivo and in culture of differentiated adult atrial cardiomyocytes from transgenic mice," Amer. J. Physiol., 259(6):H1826–H1834.

Suzuki et al., 1989, "Serum–free, chemically defined medium to evaluate the direct effects of growth factors and inhibitors on proliferation and function of neonatal rat cardiac muscle cells in culture," In Vitro Cell. Dev. Biol., 25(7):601–606.

Uyar et al., 1988, "Effects of rat platelet extracts and human platelet$\geq$derived growth factor on megakaryocytopoiesis in vitro," J. Surg. Oncol. 39:217–224.

Zak, 1984, "Factors controlling cardiac growth," Growth of the Heart in Health and Disease, Zak, R. (ed.), Raven Press, N.Y., pp. 165–185.

Claycomb et al, Developmental Biology, 127:257–265 (1988).

METHOD FOR INDUCING HUMAN MYOCARDIAL CELL PROLIFERATION

This application is a continuation of U.S. application Ser. No. 08/286,402, filed Aug. 5, 1994, now abandoned, which is a continuation of U.S. application Ser. No. 07/713,949, filed Jun. 12, 1991, now abandoned.

1. INTRODUCTION

The present invention relates to a method for inducing myocardial cell proliferation and to cell cultures produced by this method. It is based, at least in part, on the discovery that adult human myocardial cells may be induced to proliferate in culture by exposure to a platelet freeze/thaw extract.

2. BACKGROUND OF THE INVENTION

Techniques for culturing myocardial cells from rats (Harary et al., 1963, Exp. Cell. Res. 29:451–456), chicks (Friedman et al., 1987, J. Nucl. Med. 28:1453–1460), guinea pigs (Nakajima et al., 1989, Circ. Res. 64:297–303) and cats (Follmer et al., 1987, J. Physiol. 384:169–197) have been established and utilized for cardiac muscle research.

The ability to expand cultures of fetal, but not adult, human myocardial cells has been reported. Halbert et al. (1973, Life Sci. 13:969–975) observed the growth of dissociated fetal myocardiocytes in culture following previous disclosures of fetal cardiac explant cultures (Garry et al. 1948, Am. J. Physiol. 152:219–224; Chang et al., 1972, Circ. Res. 30:628–833). Claycomb et al. (1989, In Vitro Cell. Dev. Biol. 25:1114–1120), using human fetal atrial and ventricular cardiac muscle cells, established cultures of dissociated myocardiocytes with spontaneous contraction and ultrastructural characteristics of myocardial cells including organized sarcomeres, intercalated discs, and transverse tubules with couplings. Also, they demonstrated atrial granules in atrial cells and electron dense granules associated with the golgi cisternae in ventricular cells.

There have been reports of limited proliferation, or evidence of proliferative potential, of non-human myocardial cells in culture. Nag et al. in 1983 described the successful long term culture of cardiac myocytes from adult rats (Nag et al., 1983, J. Mol. Cell. Cardiol. 15:301–317) and observed morphologic changes reminiscent of embryonic or neonatal cardiac muscle cells. Earlier, Rumyantsev in 1974 reported proliferative activity of a small number of atrial myocardiocytes after experimental infarction of the left ventricle in rats while ventricular cells in the infarcted area showed no such response (Rumyantsev, 1974, Virchows Arch. B. 15:357–378). He noted that adult mammalian atrial myocardiocytes are found to proliferate in response to massive ventricular infarction, crush injury to the atrial wall, burning of the atrial wall, or hypoxia.

3. SUMMARY OF THE INVENTION

The present invention relates to a method for inducing myocardial cell proliferation. It is based, at least in part, on the discovery that adult human myocardial cells may be induced to proliferate in culture by exposure to a platelet freeze/thaw extract.

The present invention provides for a method for inducing myocardial cell proliferation in vitro, as well as for myocardial cell cultures produced by this method. In a preferred embodiment, the invention provides for human myocardial cell cultures. The myocardial cell cultures of the invention may be used to study the physiology of cardiac muscle. In addition, they may be used to identify pharmaceutical agents that may be useful in the treatment of heart disease or, alternatively, agents that are cardiotoxic. Furthermore, the cultures of the invention may be used to provide myocardial cells that may be transplanted or implanted into a patient that suffers from a cardiac disorder.

In further embodiments, the present invention also provides for a method for inducing myocardial cell proliferation in vivo. Such methods may be used in the treatment of patients suffering from cardiac disorders, particularly those who have suffered damage or loss of cardiac muscle tissue.

4. DESCRIPTION OF THE FIGURES

FIG. 1. Photomicrograph of harvested atrial cells settled at the bottom of the culture plate in 24 hours (×250).
  A) Myocardiocyte.
  B) Nonmyocardiocyte.

Figure 2:
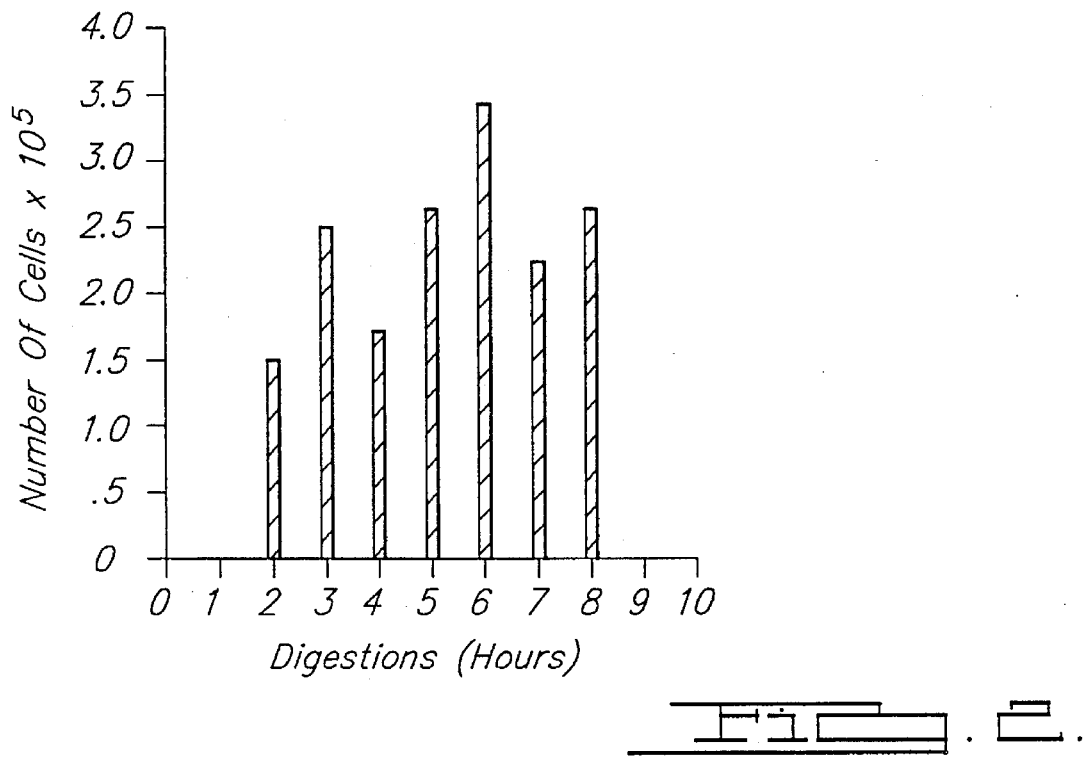

FIG. 2. Cell yield versus time of digestion. Graph comparing hemacytometric cell counts at the time of harvest for each digestion.

Figure 3:
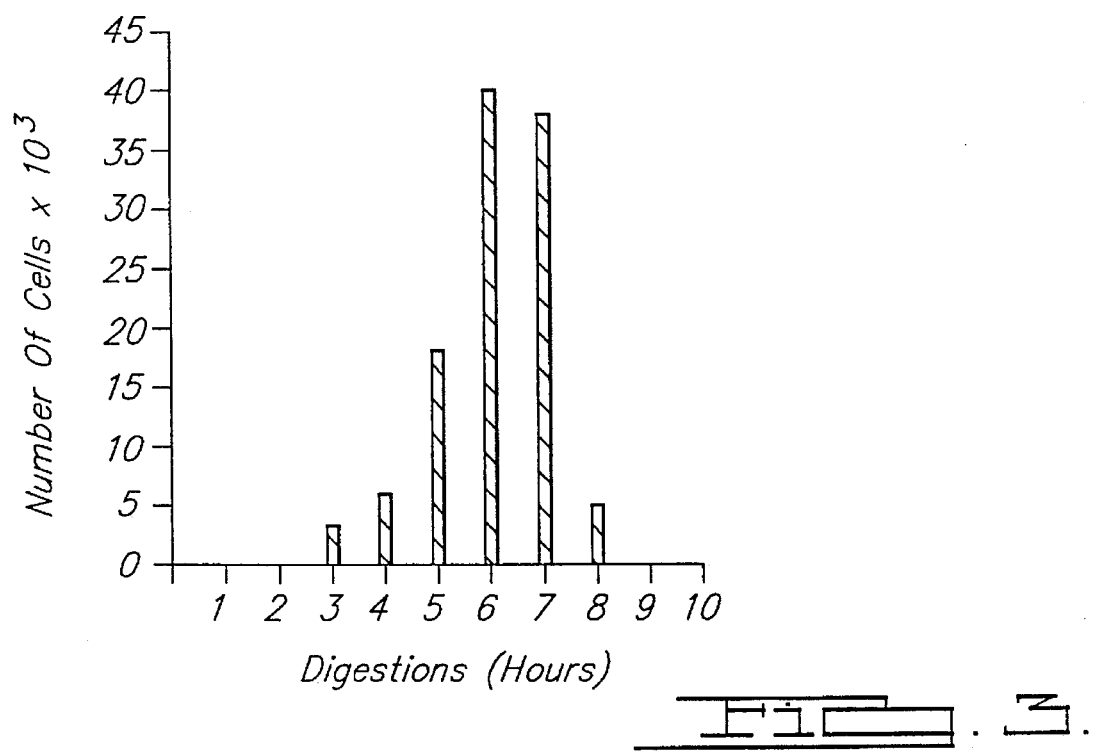
Figure 6A:
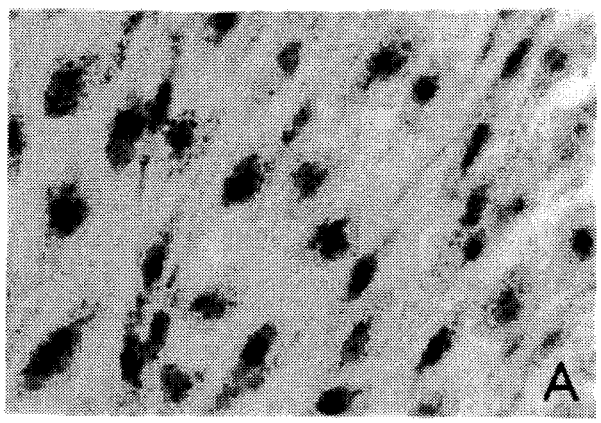
Figure 6B:
Figure 6C:
Figure 6D:
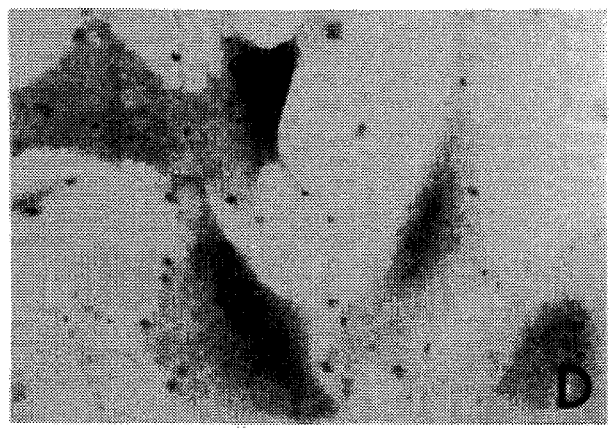
Figure 6E:
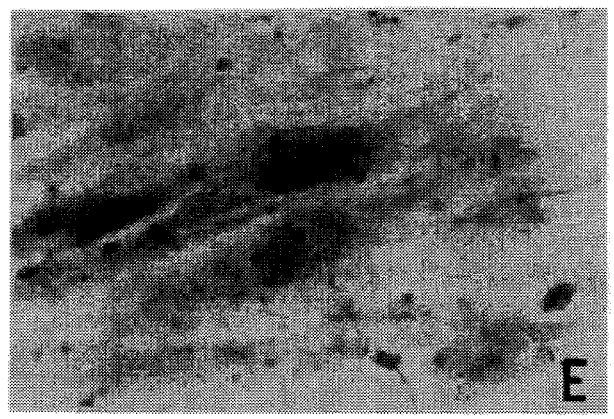
Figure 6F:
Figure 12:
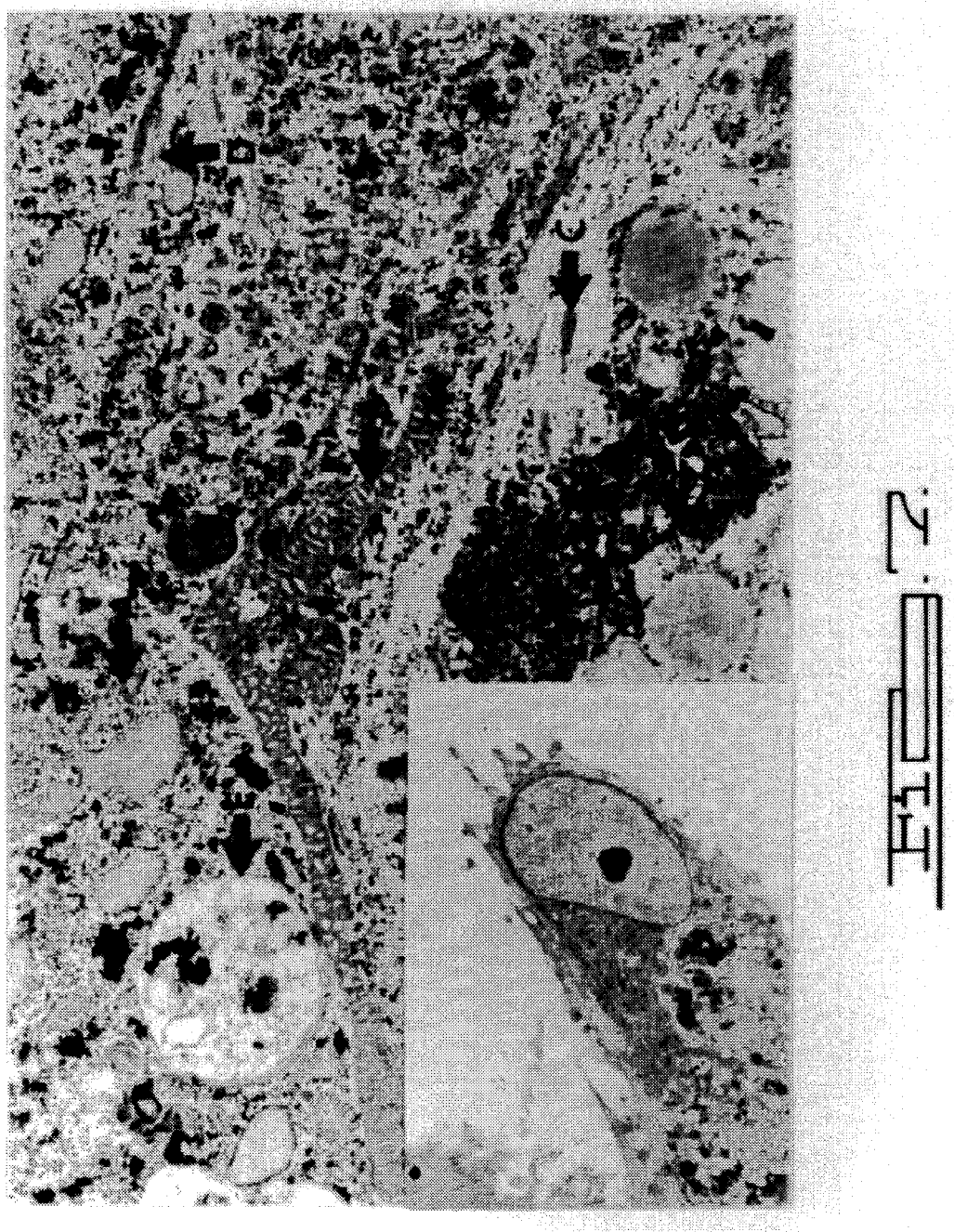

FIG. 3. Cell viability versus time of digestion. Graph comparing planimetric cell counts at one week for each digestion.

Figure 4:
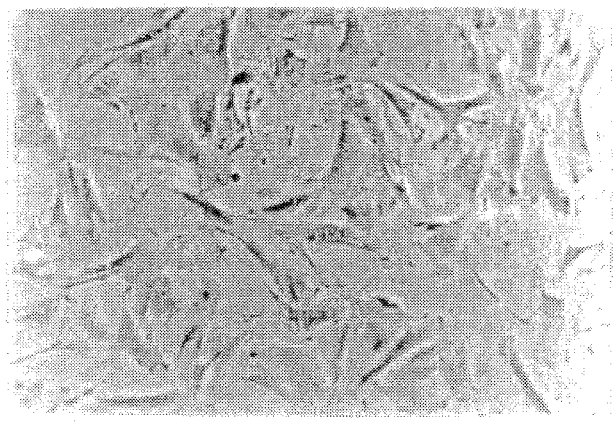

FIG. 4. Photomicrograph of cells cultured in EMEM nearing confluence, immediately before passage (×50).

Figure 5:

FIG. 5. Photomicrograph of cells cultured in MCDB 107 with characteristic "bat winged" morphology (×125).

FIG. 6. Photomicrograph demonstrating immunoperoxidase staining characteristics of presumptive myocardiocytes, control fibroblasts and control endothelial cells (×500).
  A) Endothelial cells with cytoplasmic granules staining positive for Factor VIII.
  B) Myocardiocytes negative for Factor VIII staining.
  C) Fibroblasts negative for myoglobin staining.
  D) Myocardiocytes with diffuse cytoplasmic staining positive for myoglobin.
  E) Fibroblasts with no significant actin filament staining.
  F) Myocardiocytes positive for actin filament staining.

FIG. 7. Electron micrograph of myocardiocytes cultured in MCDB 107 (×16,300; inset ×1,575).
  A) Free ribosomes.
  B) Pleomorphic mitochondria.
  C) Dense z-body with attached myofibrils.
  D) Myofibrils.
  E) Autophagosome.

5. DETAILED DESCRIPTION OF THE INVENTION

The present invention provides for a method for inducing myocardial cell proliferation and for cell cultures produced according to this method. For purposes of clarity of disclosure, and not by way of limitation, the detailed description of the invention is divided into the following subsections:
  (i) preparation of platelet freeze/thaw extract;
  (ii) methods for inducing myocardial cell proliferation in culture;
  (iii) methods for inducing myocardial cell proliferation in vivo; and
  (iv) utility of the invention.

5.1. PREPARATION OF PLATELET FREEZE/THAW EXTRACT

The platelet freeze/thaw extract of the invention may be prepared as follows. Platelets may be obtained from any suitable source. It may be desirable to use platelets originating from the same species as the myocardial cells to be treated. Platelets may be obtained from whole blood as well as apheresis units or platelet packs. Preparation should be performed at about 4° C., unless specified otherwise, so as to minimize spontaneous release of platelet α-granules.

Platelets may be removed from plasma by about 40 minute centrifugation at 1,035 RCF, and washed about 3 times by resuspending the platelets to about $5 \times 10^9$/ml with ice cold platelet buffer (such as 50 mM HEPES, 100 mM CaCl, 4 mM CaCl, 30 mM glucose, pH 6.5), followed by centrifugation for about 20 minutes. The washed platelets may then be resuspended in platelet buffer to a concentration of about $(1-10) \times 10^9$/ml. The platelets may then be frozen by placement in a dry ice bath, and then allowed to thaw. The freeze/thaw procedure may be repeated about three times. Particulate material may then be removed by centrifugation at about 1334 RCF for about 10 minutes. The resulting freeze/thaw extract may then be stored at −40° C.

The present invention also provides for the use of an active component of platelet freeze/thaw extract defined as a component of the extract that is capable of inducing myocardial cell proliferation, as well as platelet extract prepared by any method (e.g. sonication, detergent, organic solvent, or calcium ionophore) that is capable of inducing myocardial cell proliferation.

5.2. METHODS FOR INDUCING MYOCARDIAL CELL PROLIFERATION IN CULTURE

The present invention provides for a method for inducing myocardial cell proliferation in culture comprising exposing myocardial cells to an effective amount of platelet freeze/thaw extract, or an active component thereof. The myocardial cells may be obtained from any species; in preferred embodiments, the myocardial cells are obtained from a human. The myocardial cells may be atrial or ventricular. In preferred embodiments of the invention, the myocardial cells are atrial cells. The myocardial cells may be at any stage of development. In a preferred embodiment of the invention, the cells are adult myocardial cells. An effective amount of platelet freeze/thaw extract, or active component thereof is defined as that amount of extract or component which can increase the mitotic index of myocardial cells in culture, prepared as described in Section 6.1 infra by a factor of about two relative to untreated cultures. In a preferred, specific, non-limiting embodiment of the invention, the concentration of platelet freeze/thaw extract may be about one percent.

According to a preferred, specific, non-limiting embodiment of the invention, myocardial cells may be prepared and cultured according to methods set forth in Example 6, infra, which, briefly, are as follows. Fresh myocardial tissue may be minced into small (about 0.5–1.0 mm³) pieces and placed in cold buffer such as Hank's Balanced Salt Solution (HBSS) without calcium or magnesium. The minced myocardial tissue may then be digested in collagenase solution at an enzyme concentration of about 1.43 mg/ml at 37° C. As shown in FIG. 3, optimal cell viability may be achieved by digesting the tissue for about six hours. The resulting cells may be removed from supernatant by centrifugation at 3500 RPM for about 10 minutes at 37° C. The cell pellet may then be resuspended in a suitable volume of appropriate medium, such as Earle's Minimal Essential Medium (EMEM) with Earle's salts containing about 10% newborn calf serum and 0.1% antibiotic solution (e.g. 10,000 units/cc Penicillin G, 10,000 μc/cc Streptomycin and 25 μg/cc Amphotericin B). The cells may then be further adjusted with EMEM to a concentration of about $1 \times 10^5$ cells/ml, plated on gelatin coated dishes, and incubated at 37° C. in a 5% $CO_2$ atmosphere. To produce proliferating myocardial cell cultures, the cells may alternatively be placed in serum-free myocardial selective MCDB 107 medium containing about 1% platelet freeze/thaw extract or an effective concentration of the extract or active component. Cells should be fed with fresh medium about every 3–5 days.

In still further embodiments, myocardial cells present in cardiac tissue explants may be cultured in vitro by exposure to effective amounts of platelet freeze/thaw extract, as outlined above.

5.3. METHODS FOR INDUCING MYOCARDIAL CELL PROLIFERATION IN VIVO

The present invention also provides for a method for inducing myocardial cell proliferation in vivo comprising administering, to a patient in need of such treatment, an effective amount of platelet freeze/thaw extract or an active component thereof. An effective amount may be determined in vitro, as described above, and then be adjusted for in vivo use according to methods known in the art.

The extract or its active component may be administered by any suitable method, either systemically or locally, by injection or direct application. In a specific embodiment, the extract or its active component may be administered by way of an implant, such as a sustained release device that may gradually release extract or its active component. Such an implant may be particularly useful in promoting local proliferation of myocardial cells.

A patient, as described herein, may be human or non-human, including, for example, a rodent, horse, primate, bovine, ovine, or porcine subject.

5.4. UTILITY OF THE INVENTION

The present invention provides for the preparation of long term, proliferating myocardial cell cultures. Such cultures may be used to evaluate pharmaceutical agents for an ability to promote the growth, survival, or functional activity (e.g. contractility) of myocardium. Alternatively, such cultures may be used to evaluate agents for the capability of inducing deleterious effects in myocardium. Putative therapeutic or, alternatively, toxic agent may be administered in serial dilutions to multiple myocardial cultures produced by the method of the invention, and the $ED_{50}$ or $TD_{50}$ may be calculated using standard techniques.

In further embodiments, myocardial cells may be expanded in culture by the methods of the invention and then implanted or transplanted into a patient in need of such treatment. In this manner, autologous or heterologous cells may be implanted or transplanted into a patient who suffers from a cardiac disorder. As one specific example, cells may be implanted into a patient who has suffered a myocardial infarction prior to the onset of fibrosis, therefore potentially avoiding a weakening in the myocardium that may result in aneurysm formation. Alternatively, such cells, or artificially produced myocardial tissue, may be used in aneurysm repair. In further embodiments, cells generated in culture may be used in conjunction with artificial materials to produce substrates for reconstructive cardiac surgery.

In further specific embodiments, atrial myocardial cells caused to proliferate by the methods of the invention may be used in vivo or in vitro as a source of atrial natriuretic peptide. A cellular implant comprising such cells may be introduced into a patient as a source of atrial natriuretic peptide that is subject to biofeedback mechanism.

6. EXAMPLE: A METHOD FOR THE HARVEST, CULTURE, CHARACTERIZATION AND PROLIFERATION OF HUMAN ADULT MYOCARDIAL CELLS

6.1. MATERIALS AND METHODS

6.1.1. CELL HARVEST

Atrial tissue was obtained from right atrial appendages harvested from cardiovascular surgery patients undergoing procedures requiring "heart-lung bypass." The patients were randomly selected and included both sexes, with ages ranging from 44 to 73 years old. These atrial appendages were removed routinely in order to insert the venous cardiopulmonary bypass cannulae into the right atria. They were obtained for study immediately after removal and placed in ice-saline slush. After rinsing in saline, the tough epicardial covering was removed using a scalpel to reduce the amount of connective tissue included in the cell harvest. The remaining "pure" atrial muscle was minced into small (0.5–1.0 mm$^3$) pieces and placed in cold Hank's Balanced Salt Solution (HBSS) without calcium or magnesium (Whittaker, Walkerville, Mass.). The atrial pieces were then transported from the operating suite to the tissue culture laboratory.

6.1.2. DIGESTION AND PLATING

The minced atrial tissue was digested in collagenase solution (Worthington, Freehold, N.J.) at a concentration of 1.43 mg/ml. The pieces were placed in 35 ml of this solution and digested in a shaker at 37° C. at 125 RPM for one hour. The supernatant was removed from the atrial tissue and centrifuged at 3500 RPM for 10 minutes at 37° C. Another 35 ml of collagenase solution was placed with the minced tissue while the supernatant was spinning and the digestion continued for another hour. The cell suspension formed a pellet during centrifugation. The supernatant collagenase solution was removed and set aside for use in the third digestion. The cell pellet was resuspended in 2 ml of Eagle's Minimal Essential Medium (EMEM) with Earle's Salts (Whittaker) containing 10% newborn calf serum (Whittaker) and 0.1% antibiotic solution (10,000 units/cc Penicillin G, 10,000 μg/cc Streptomycin and 25 μg/cc Amphotericin B (Gibco, Grand Island, N.Y.)). This process was continued for a total of 8 digestions. The first pellet was discarded and digestions 2–8 pooled. The cell concentration was checked using a hemacytometer and adjusted to 1×10$^5$ cells/ml with EMEM. The cells were plated on 35mm gelatin coated dishes (Corning, Corning, NY) and incubated at 37° C. in 5% CO$_2$ atmosphere. Medium was changed every three days for the first two weeks of growth, then every five to seven days thereafter. When the cultures spread out and approached confluence, they were treated with trypsin and transferred to 60 mm gelatin coated dishes (Corning) in EMEM. As the cultures again spread out and approached confluence they were treated with trypsin and transferred to T–75 flasks (Corning) in MCDB 107 (Sigma, Saint Louis, Mo.).

6.1.3. IMMUNOPEROXIDASE STAINING

A portion of the cells grown in MCDB 107 were plated in four-chamber gelatin coated slide culture plates (Lab Tek, Naperville, Ill.) along with human endothelial cell and fibroblast cultures (Beaumont Research Institute, Royal Oak, Mich.) used as controls. When control cultures and harvested cells spread out and approached confluence they were rinsed with HBSS and fixed with 10% formalin for 10 minutes. The chambers were removed and the cells remaining on the plates were stained with monoclonal antibody peroxidase stains for actin (Sigma), myosin (Sigma), myoglobin (Dako, Carpinteria, Calif.) and factor VIII (Lipshaw, Detroit, Mich.). The plates were then examined using light microscopy.

6.1.4. ELECTRON MICROSCOPY

A portion of harvested cells in MCDB 107 were plated on 96 well gelatin coated plates (Corning). When they spread out and approached confluence they were rinsed with HBSS and fixed with 2.5% glutaraldehyde/0.2M cocodylate buffer (Polysciences, Inc., Warrington, Pa.) at a pH of 7.4, post-fixed with 1% osmium tetroxide (Polysciences, Inc.), embedded in Epon LX-112 resin (Ladd's Research, Burlington, Va.), stained with 0.03% lead citrate (Eastman Kodak, Rochester, N.Y.) and saturated uranyl acetate (Pelco Co., Tustin, Calif.) in 50% ethyl alcohol and then examined under transmission electron microscopy.

6.1.5. PLATELET RELEASATES

Platelets were obtained as apheresis units or platelet packs. All steps were done at 4° C., unless otherwise specified, to minimize spontaneous release of platelet s-granules. Platelets were removed from plasma by 40 minute centrifugation at 1,035 RCF, and washed three times by resuspending the platelets to approximately 5×10$^9$/ml with ice cold platelet buffer (50 mM HEPES, 100 mM CaCl, 4 mM KCl, 30 mM glucose, pH 6.5) followed by a 20 minute centrifugation. Samples of washes were centrifuged for one hour at 3,000 RCF to remove any residual platelets and retained for analysis. The washed platelets were resuspended in platelet buffer and adjusted to the desired concentration (1–10×10$^9$/ml). Preparations were then subdivided for different release procedures: 1) the thrombin releasates (TR) were prepared by incubating platelets with bovine thrombin from Armor (1 unit/10 platelets) for 10 minutes at room temperature; 2) freeze/thawed releasate (FTR) were prepared by repeated freezing of the platelets in a dry ice bath three times; 3) the Triton X100 releasates (TXR) were prepared by addition of Triton X100 to a final concentration of 0.1–1.0% (no differences were observed within this range of Triton X100). Particulate material was centrifuged at 1334 RCF for 10 minutes. Material was stored at −40° C.

6.1.6. TREATMENT WITH GROWTH FACTORS

A myocardial cell culture, obtained using methods outlined supra, was 93% pure with 4% smooth muscle contaminants and 3% fibroblast contaminants. The cells were split equally onto culture plates at approximately 10% confluence. All cells were grown in serum-free MCDB 107 medium, which is selective for myocardiocytes. Five plates were used as a negative control and left untreated, five plates were treated with a platelet freeze/thaw preparation at a final concentration of 1% and five plates were treated with 1 nM endothelin-1. Daily planimetric cell counts were carried out at four standard locations on each plate. At the conclusion of the study, actin immunoperoxidase stains were used to evaluate the proportion of contaminating non-myocardial cells. Bromo-deoxyuridine incorporated into the nuclear DNA was carried out to determine the number of cells undergoing DNA replication and this number was used to calculate the mitotic index.

6.2. RESULTS

6.2.1. SETTLING AND ATTACHMENT

Suspended cells settled very quickly. Usually within one hour after plating, the majority of harvested cells were seen on the bottom of the culture dish; they were not adherent, however, as gentle agitation resuspended them. They required 48–72 hours before attachment and cytoplasmic spreading occurred. This is consistent with the experience of Nag et al., (1983, J. Mol. Cell. Cardiol. 15:301–317) culturing adult rat myocardiocytes. The settled cells were inspected using phase contrast microscopy and categorized as myocardial or nonmyocardial on the basis of their appearance. Myocardial cells were rectangular or spindle shaped, and had cross striations, a single nucleus with prominent nucleolus and occasional branching. Nonmyocardial cells were round or oval shaped and lacked clearly identifiable cross striations (FIG. 1). The yield of cells averaged 42.8% myocardial and 57.2% nonmyocardial.

6.2.2. CELL YIELDS

Cell yields, including both myocardial and nonmyocardial cells, were relatively constant for digestions 2–8 (FIG. 2). Cell counts ranged from $1.5 \times 10^5$/ml at two hours to $3.4 \times 10^5$/ml at six hours. Cell viability, however, varied with the length of digestion (FIG. 3). Planimetric cell counts measured at one week for cultures plated separately for each digestion showed a steady increase in cell viability in digestions one through seven, peaking at six to seven hours then dropping abruptly after that, so that viability was nil at nine hours or more of digestion.

6.2.3. GROWTH CHARACTERISTICS

After attaching to the gelatin matrix, the cells spread out with numerous cytoplasmic extensions seen extending from them. Within two weeks of plating, the cells had sufficiently spread to reach confluence (FIG. 4). "Splitting" the cells and transferring them to 60 mm dishes and then T-75 flasks resulted in similar spreading to reach confluence. Utilizing EMEM the maximum number of passages made was six. Using MCDB 107, a medium shown by Suzuki et al. (1989, In Vitro Cell. Dev. Biol. 25:601–606) to be selective for the growth of myocardial cells, the maximum number of passages dropped to three. The phase contrast microscopic appearance of cells cultured in MCDB 107 was described as "bat winged" (FIG. 5) and was similar to cells seen in human fetal atrial myocardial cell cultures (Claycomb et al., 1989, In Vitro Dev. Biol. 25:1114–1120).

6.2.4. CHARACTERIZATION

Monoclonal antibody immunoperoxidase stains were performed on presumptive myocardiocytes using human fibroblasts and endothelial cells as controls. The stains showed characteristic staining of harvested cells for the striated muscle proteins actin, myosin and myoglobin while control cells did not. Factor VIII stains of endothelial cells highlighted their characteristic cytoplasmic granules while the same stains revealed no such granules in the presumptive myocardiocytes. Actin stains in the presumptive myocardiocytes demonstrated numerous cytoplasmic filaments while myoglobin stains showed more diffuse cytoplasmic staining (FIG. 6). Electron microscopy of the myocardiocytes revealed that they were secretory cells containing numerous free ribosomes, rough endoplasmic reticulum and secretory granules. The cells also contained numerous microfilaments. No well organized sarcomeres or t-tubules were seen; however, dense z-bodies containing attached microfilaments and pleomorphic mitrochondria were prominent (FIG. 7). The electron micrographic appearance was similar to that seen in adult rat myocardiocyte cultures at 14 days undergoing myofibrillar reorganization (Nag et al., 1983, J. Mol. Cell. Cardiol. 15:301–317).

6.2.5. STIMULATION OF PROLIFERATION BY PLATELET FREEZE/THAW EXTRACT

Initial planimetric cell counts averaged 862±88, 856±97 and 888±75 cells per plate for control, platelet preparation and endothelin treated cells respectively. Planimetric cell counts after 10 days in culture averaged 1010±100, 2090±360 and 1000±96 cells per plate respectively. Control cells increased their population by 16% (p=0.03), platelet preparation treated cells increased their population by 144% (p=0.001) and endothelin treated cells increased their population by 12% (p=0.04). A comparison of the mitotic indices, corrected for contaminants, of control cells and platelet preparation treated cells was 0.33% versus 1.6% (p=0.0003). The 5-fold increase in the mitotic index for cells cultured with the platelet growth factor preparation indicates that a mitogenic factor exists in this preparation for myocardiocytes.

6.3. DISCUSSION

Atrial myocardiocytes represent a heterogeneous population of cells. The common atrial myocyte is specialized not only as a contractile muscle cell but also as an endocrine cell secreting atrial natriuretic peptide (ANP). This hormone has potent diuretic and hypotensive effects and inhibits renin and aldosterone secretion (DeBold, 1985, Sci. 230:767; Flynn et al., 1985, Biochem. J., 232:313). Atrial myocytes therefore have the machinery responsible for synthesis, processing and releasing ANP. The specific organelles involved are rough endoplasmic reticulum, free ribosomes, Golgi apparatus and atrial specific granules. Other ultrastructural details unique to atrial myocytes are 1) absent or few transverse tubules and 2) tremendous variation in the organization of sarcomeres, from dense and well organized, as seen in ventricular cells, to scanty and haphazard (Severs et al., 1989, "Isolated Adult Cardiomyocytes" H. M. Piper and G. Isenberg eds., Vol. 1, Boca Raton, CRC Press).

We have found no published reports of adult human myocardial cell culture systems. The above-mentioned culture results required great persistence in developing and optimizing methods of harvest and digestion. It also had to be ascertained that the cultured cells were, in fact, myocardial cells rather than fibroblasts. Immunoperoxidase stains were performed that suggested that the growing cells were of cardiac muscle origin. Repeat stains on the same harvest and stains of additional cell harvests verified these findings. Transmission electron microscopy (TEM) confirmed the muscular origin of these cells. We found ultrastructural organization consistent with adult rat myocardial cells undergoing myofibrillar reorganization as observed by Nag et al. (1983, J. Mol. Cell. Cardiol. 15:301–317).

Myocardial injury in mammals is primarily repaired by fibrosis and scarring. In such injuries no ventricular and only limited atrial myocardiocyte proliferation occurs. As described above, we have conducted in vitro studies of atrial myocardiocytes, treating them with a variety of growth factors. Atrial myocardiocytes were grown from explanted human adult tissue and separated using selective attachment techniques. The cells were characterized using immunoperoxidase staining with actin, myoglobin and atrial natriuretic peptide antibodies. It was found, surprisingly, that culturing the atrial myocardiocytes together with platelet freeze/thaw extract had a mitogenic effect, leading to a 144 percent increase in cell number and a 5-fold increase in the mitotic index.

Various publications are cited herein that are hereby incorporated by reference in their entirety.

What is claimed is:

1. A method for inducing human adult myocardial cell proliferation in vitro, comprising:

adding platelet freeze/thaw extract, in amount effective to induce proliferation, to a culture of human adult myocardial cells.

2. The method of claim 1, wherein said adult myocardial cells are atrial cells.

3. The method of claim 1, wherein said amount effective to induce proliferation is about one percent platelet freeze/thaw extract.

4. A method for inducing human adult myocardial cell proliferation in vitro, comprising:

culturing human adult myocardial cells in a tissue culture medium comprising about one percent platelet freeze/thaw extract.

\* \* \* \* \*